United States Patent [19]
Pfäffli

[11] Patent Number: 4,791,116
[45] Date of Patent: Dec. 13, 1988

[54] N,N-DIETHYL-N'-[(8α)-1-ETHYL-6-METHYL-ERGOLIN-8-YL]-SULFAMIDE USEFUL AS PROLACTIN SECRETION INHIBITOR, ANTI-PARKINSON AGENTS AND ANTI-DEPRESSANT AGENTS

[75] Inventor: Paul Pfäffli, Oberwil, Switzerland
[73] Assignee: Sandoz Ltd., Basel, Switzerland
[21] Appl. No.: 936,204
[22] Filed: Dec. 1, 1986

Related U.S. Application Data

[63] Continuation of Ser. No. 846,699, Apr. 1, 1986, abandoned, which is a continuation of Ser. No. 579,030, Feb. 10, 1984, abandoned.

[30] Foreign Application Priority Data

Feb. 16, 1983 [CH] Switzerland ........................... 863/83
Feb. 16, 1983 [CH] Switzerland ........................... 862/83

[51] Int. Cl.$^4$ ..................... A61K 31/48; C07D 457/12
[52] U.S. Cl. ......................................... 514/288; 546/68
[58] Field of Search .......................... 546/68; 514/288

[56] References Cited

U.S. PATENT DOCUMENTS

| | | | |
|---|---|---|---|
| 4,348,391 | 9/1982 | Stütz et al. | 546/68 |
| 4,348,392 | 9/1982 | Fehr et al. | 546/68 |
| 4,690,929 | 9/1987 | Bernardi et al. | 546/68 |

FOREIGN PATENT DOCUMENTS

| | | | |
|---|---|---|---|
| 82808 | 6/1983 | European Pat. Off. | 546/68 |
| 622518 | 4/1981 | Switzerland | 546/68 |
| 628895 | 3/1982 | Switzerland | 546/68 |

*Primary Examiner*—Donald G. Daus
*Assistant Examiner*—Cecilia Shen
*Attorney, Agent, or Firm*—Gerald D. Sharkin; Robert S. Honor; Thomas O. McGovern

[57] ABSTRACT

The present invention provides N,N-Diethyl-N'-[(8α)-1-ethyl-6-methyl-ergolin-8-yl]-sulfamide, and N,N-Diethyl-N'-[(8α)-1-isopropyl-6-methyl-ergolin-8-yl)-sulfamide useful as prolactin secretion inhibiton, antiparkinson agents and anti-depressant agents.

4 Claims, No Drawings

N,N-DIETHYL-N'-[(8α)-1-ETHYL-6-METHYL-ERGOLIN-8-YL]-SULFAMIDE USEFUL AS PROLACTIN SECRETION INHIBITOR, ANTI-PARKINSON AGENTS AND ANTI-DEPRESSANT AGENTS

This is a continuation of application Ser. No. 846,699, filed 4/1/86, now abandoned, which in turn is a continuation of Ser. No. 579,030, filed 2/10/84, now abandoned.

This invention relates to ergot derivatives. U.S. Pat. No. 4,348,391 discloses a broad class of (8α)ergoline-8-ylsulfamides as anti-parkinson agents, anti-depressant agents and prolactin secretion inhibitors. All the specifically exemplified compounds have an allyl group or a methyl group in the 1 position. We have now found that the following compounds of formula I which have not been specifically suggested or disclosed in this patent have an exceptionally interesting pharmacological profile, inter alia prolonged activity, especially as anti-parkinson agents, and are well tolerated, especially on oral application, as described in the tests hereinafter.

The present invention provides a compound of formula I

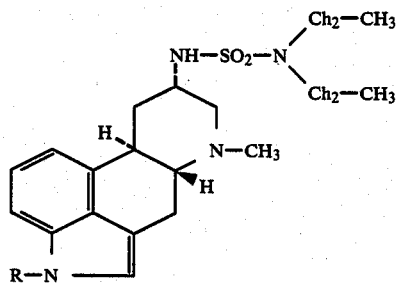

wherein R is ethyl or isopropyl. Such compounds may be in the form of the free base or in the form of an acid addition salt.

In another aspect the present invention provides a process for the production of a compound of formula I as defined above in free base form or in the form of an acid addition salt, which comprises alkylating a compound of formula II

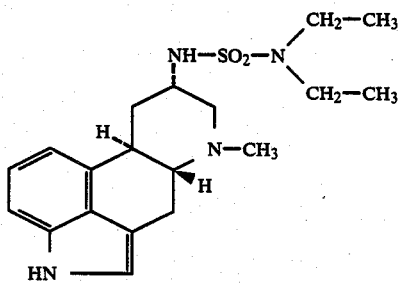

and recovering the resultant compound in free base form or in the form of an acid addition salt.

The process may be effected in conventional manner for the alkylation of the indole nitrogen in analogous compounds. For example a compound of forumal III

R—X                                          III wherein X is the acid radical of a reactive ester, for example halogen, e.g. iodine or an organic sulfonic acid radical, may be used as alkylating agent.

The reaction may be effected in a solvent, e.g. liquid ammonia, at from about −40° C. to the boiling temperature, if desired in the presence of a base, e.g. sodium butoxide or iron trichloride.

The resultant compound of formula I may be isolated and purified in conventional manner.

Free base forms of the compounds of formula I may be converted in conventional manner into the acid addition salt forms and vice versa. Compounds of formula II are known.

In the following examples all the temperatures are in degrees Centigrade.

EXAMPLE 1

N,N-Diethyl-N'-[(8α)-1-ethyl-6-methyl-ergolin-8-yl]-sulfamide 1.61 g (70 mM) sodium metal are added portionwise to a mixture of 35 mg (0.22 mM) iron trichloride, 7.52 ml (80 mM) tert butyl alcohol and 40 ml ammonia, which is stirred and cooled with dry ice, 7.53 g (20 mM) N,N-diethyl-N'-[8α)-6-methyl-ergolin-8-yl]-sulfamide are then added. 1.938 ml (24 mM) ethyl iodide are added dropwise over 4 hours to the reaction mixture under reflux. The reaction mixture is stirred under reflux for a further 3 hours.

The ammonia is allowed to evaporate overnight under stirring. The reaction mixture is allowed to warm to room temperature and is partitioned between 80 ml 2M aqueous ammonium sulphate solution and methylene chloride. The organic extracts are washed, dried with sodium sulphate, concentrated and applied to a chromatography column (silicagel 170 g) with toluenene/methanol (98/2). The title compound is eluted and crystallised from toluene/hexane (50:50). M.pt. 101°–102°; $[\alpha]_D^{20} = -64.6°$ (c=1.018% in Chloroform).

In analogous manner to that described in Example 1 the following compound is produced:

EXAMPLE 2

N,N-Diethyl-N'-[(8α)-1-isopropyl-6-methylergolin-8-yl]sulfamide

M.pt. 108°–110°; $[\alpha]_D^{20} = -63.5°$ (1.038% in Chloroform).

The compounds of formula I in free base form or in the form of a pharmaceutically acceptable acid addition salt exhibit pharmacological activity and are therefore useful as pharmaceuticals, e.g. for therapy.

In particular the compounds are useful as central dopamine receptor agents for the treatment of e.g. Morbus Parkinson as indicated in standard tests. For example in rates lesioned unilaterally in the nigro-neostratal dopamine pathway by the effect of a 6-hydroxy-dopamine injection in the substantia nigra the compounds at doses of between about 3 and about 30 mg/kg p.o., according to the method of U.Ungerstedt Acta.physiol.scand.Suppl.387, 69–93 (1971) and substantially the same as that described by J. M. Vigouret et al., Pharmacology 16 (Suppl.1) 156–193 (1978), induce turning in the direction of the non-denerved side over a long period of time, e.g. several hours.

The compounds are therefore useful as anti-parkinson agents. The example 1 compound has anti-parkinson activity as the preferred indication, and has particularly patent anti-parkinson activity relative to prolactin secretion activity in tests described herein.

Furthermore, the compounds exhibit anti-depressant activity in conventional tests, e.g. by an inhibition of the akinesia induced by reserpine in the rat at doses of from about 0.5 to about 10 mg/kd s.c. of the compounds and by an inhibition of the akinesia induced by tetrabenzine in the rat at doses of from about 10 to 30 mg/kg p.o. of the compounds. The method is based on that described by J. M. Vigouret et al., Pharmacology 16 (Suppl.1) 156–193 (1978).

The compounds are therefore useful additionally as anti-depressant agents.

Additionally the compounds inhibit prolactin secretion as indicated in standard tests, e.g. as described by E. Flückiger et al, Experienta 34, 1330–1332 (1978).

For example the compounds inhibit implantation in female rats on subcutaneous application of from about 0.03 and about 3 mg/kg s.c. and inhibit prolactin secretion in male rats on p.o. application of doses from about 0.001 to about 0.5 mg/kg according to the method of Flückiger et al, Postgraduate Medical School Journal 52, Suppl.1, 57 (1976). The effects are for an unexpectedly long period e.g. several hours.

The compounds are therefore useful as prolactin secretion inhibitors e.g. for hyperprolactinea associated disorders. The Example 2 compound is the preferred compound for this indication.

For all these uses the dosage will, of course, vary depending on the compound employed, mode of administration and treatment desired. However, in general, satisfactory results are obtained when administered at a daily dosage of from about 0.001 mg to about 30 mg per kg animal body weight, conveniently given in appropriate 1 to 4 times a day or in sustained release form. For the larger mannal, the total daily dosage is in the range from about 0.5 to about 100 mg, and dosage forms suitable for oral administration comprise from about 0.1 mg to about 50 mg of the compounds admixed with a solid or liquid pharmaceutical carrier or diluent.

The compounds are indicated to be well tolerated on the basis of pharmacological tests.

For example in the infusion cat test the fall in blood pressure and drop in heart rate was less than expected at doses of about 37 micrograms/kg i.v. and thus the compounds are indicated to be well tolerated from the cardiovascular standpoint.

Additionally the compounds show satisfactory tolerability at 0.3 mg/kg/day p.o. in the beagle dog, and the compound of example 1 leads to few emetic effects.

The compounds also show a protracted onset of activity of the above anti-parkinson, anti-depressant and prolactin secretion inhibition tests on oral administration indicating a reduction of, e.g. initial, side effects, e.g. emesis.

The example 1 compound is preferred. The anti-parkinson activity is the preferred indication.

Thus compounds of formula I may be administered in similar manner to known standards for the same indications, e.g. bromocryptine. The suitable daily dosage for a particular compound to be administered will depend on a number of factors inter alia potency.

Thus the preferred compound, the example 1 compound, has for example the following activities in the tests:

|  | Ungerstedt test No of rotations at 3 mg/kg p.o.[1] | ED$_{50}$ Implantation mg/kg s.c. |
|---|---|---|
| Example 1 | 774 | 0.23 |
| Example 2 | 1608 | 0.08 |
| Bromocriptine | 80[2] | 0.75 |

[1]Over 7 hours;
[2]at 0.1 mg/kg s.c.

It is therefore indicated that the compounds of formula I may be administered at the same order of dosages as bromocryptine.

Naturally to find the optional therapeutic dose in any particular subject the lowest dosage, e.g. 0.5 may be first tried and the dosage increased until the desired effect is observed. Representative oral doses may be up to 20 mg and for the anti-parkinson indication up to 75 mg, because the compounds are well tolerated.

The compounds may be administered in the form of a pharmaceutically acceptable acid addition salt form. Such salt forms have the same order of activity as the free base form. The present invention accordingly provides a compound of formula I in free base form or in pharmaceutically acceptable salt form in association with a pharmaceutical carrier or diluent. Such compositions may be formulated in conventional manner so as to be for example a solution or a tablet.

What we claim is:
1. A compound of formula I

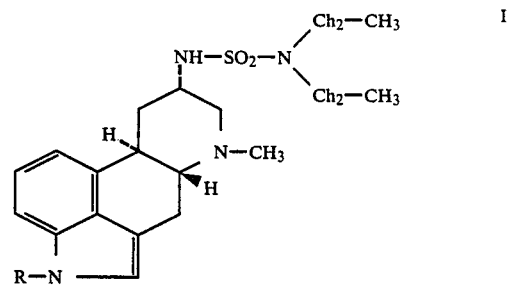

where R is ethyl in free base form or in the form of a pharmaceutically acceptable acid addition salt.

2. A pharmaceutical composition useful for inhibitin prolactin secretion, treating depression or Morbus Parkinson comprising an effective amount of a compound according to claim 1 in association with a pharmaceutical carrier or diluent.

3. A method of inhibiting prolactin secretion, treating depression or Morbus Parkinson in a subject which comprises administering a therapeutically effective amount of a compound of claim 1 to a subject in need of such treatment.

4. The compound of claim 1, which is N,N-Diethyl-N'-[(8α)-1-ethyl-6-methyl-ergolin-8-yl]-sulfamide.

* * * * *